(12) United States Patent
Natori et al.

(10) Patent No.: US 7,787,178 B2
(45) Date of Patent: Aug. 31, 2010

(54) OBJECTIVE-LENS GUIDING DEVICE AND OBJECTIVE LENS UNIT

(75) Inventors: Yasuaki Natori, Tokyo (JP); Masato Fujiwara, Tokyo (JP); Nobuhiko Onda, Tokyo (JP); Tatsuya Okadome, Tokyo (JP); Ikuko Sakai, Tokyo (JP)

(73) Assignee: Olympus Corporation, Tokyo (JP)

(*) Notice: Subject to any disclaimer, the term of this patent is extended or adjusted under 35 U.S.C. 154(b) by 377 days.

(21) Appl. No.: 11/894,507

(22) Filed: Aug. 20, 2007

(65) Prior Publication Data
US 2008/0051666 A1    Feb. 28, 2008

(30) Foreign Application Priority Data
Aug. 25, 2006   (JP) ............................. 2006-229719

(51) Int. Cl.
   *G02B 21/00* (2006.01)
   *G02B 21/02* (2006.01)
(52) U.S. Cl. .................. 359/379; 359/368; 359/656
(58) Field of Classification Search ......... 359/368–390, 359/656–661, 819
   See application file for complete search history.

(56) References Cited
U.S. PATENT DOCUMENTS

| 1,889,794 | A | * | 12/1932 | Sarel | 359/829 |
| 3,837,731 | A | * | 9/1974 | Amos et al. | 359/656 |
| 4,682,859 | A | * | 7/1987 | Togino et al. | 359/656 |
| 5,501,217 | A | | 3/1996 | Ishiguro et al. | |
| 2008/0049311 | A1 | * | 2/2008 | Hirata | 359/379 |

FOREIGN PATENT DOCUMENTS

| EP | 1 524 542 | 4/2005 |
| JP | 2005-121947 | 5/2005 |
| WO | WO 95/10218 | 4/1995 |

* cited by examiner

*Primary Examiner*—Thong Nguyen
(74) *Attorney, Agent, or Firm*—Kenyon & Kenyon LLP

(57) ABSTRACT

Without setting an examination site, it is possible to easily position an end face of a narrow-diameter end portion at a suitable position with respect to an examination target, allowing an image of the examination site to be acquired quickly and easily. The invention provides an objective-lens guiding device comprising a support portion secured to an objective lens having a narrow-diameter end portion; and a cylindrical portion for accommodating the narrow-diameter end portion. The support portion supports the cylindrical portion such that a front end of the cylindrical portion is disposed at a location farther toward the front than an end face of the narrow-diameter end portion, and so as to be capable of moving in an optical axis direction.

7 Claims, 8 Drawing Sheets

OBJECTIVE-LENS GUIDING DEVICE AND OBJECTIVE LENS UNIT

BACKGROUND OF THE INVENTION

1. Field of the Invention

The present invention relates to an objective-lens guiding device and to an objective lens unit.

This application is based on Japanese Patent Application No. 2006-229719, the content of which is incorporated herein by reference.

2. Description of Related Art

To obviate the need for positioning which must be carried out each time the interior of a small laboratory animal or the like is observed, there is a known technique in the related art involving securing an objective-lens insertion tool, into which an objective lens can be inserted and adjusted in position, to the skin of the small laboratory animal under examination (for example, see Japanese Unexamined Patent Application, Publication No. 2005-121947).

However, with the objective-lens insertion tool described in Japanese Unexamined Patent Application, Publication No. 2005-121947, by securing the objective-lens insertion tool to the examination object once an examination site inside the small laboratory animal under examination is set, it is possible to carry out observation while positioned at the same location, even when repeatedly attaching and detaching the objective lens. However, during the process of searching for the examination site, it is necessary to perform focusing each time. In addition, when observing the surface of an internal organ or the like with a narrow-diameter end portion provided at the end of the objective lens inserted inside the living organism, the end face of the narrow-diameter end portion is inserted inside the living organism and thus cannot be seen from outside. Therefore, it is not possible to accurately determine the positional relationship with the surface of the internal organ or the like, resulting in the drawback that focusing at the surface of the internal organ or the like must be performed by trial and error.

BRIEF SUMMARY OF THE INVENTION

The present invention has been conceived in light of the circumstances described above, and an object thereof is to provide an objective-lens guiding device and an objective lens unit in which the end face of a narrow-diameter end portion can be easily located at a suitable position relative to an examination target, without setting an examination site, thus enabling rapid and straightforward acquisition of an image of the examination site.

In order to realize the object described above, the present invention provides the following solutions.

A first aspect of the present invention is an objective-lens guiding device including a support portion secured to an objective lens having a narrow-diameter end portion; and a cylindrical portion configured to accommodate the narrow-diameter end portion, wherein the support portion supports the cylindrical portion so that a front end of the cylindrical portion is disposed at a location farther toward the front than an end face of the narrow-diameter end portion, and so as to be capable of moving in an optical axis direction.

According to the first aspect of the present invention, by securing the objective-lens guiding device to the objective lens, the front end of the cylindrical portion which accommodates the narrow-diameter end portion is disposed further towards the front than the end face of the narrow-diameter end portion. Therefore, when the cylindrical portion and the narrow-diameter end portion are inserted inside the body of the examination target, such as a small laboratory animal, the front end of the cylindrical portion initially abuts against the surface of the examination site inside the body. Because the cylindrical portion is supported by the support portion so as to be capable of moving in the optical axis direction, by setting the front end of the cylindrical portion and the end face of the narrow-diameter end portion to have a predetermined distance therebetween, it is possible to locate the end face of the narrow-diameter portion at a suitable distance relative to the surface of the examination site simply by abutting the front end of the cylindrical portion against the surface of the examination site. Thus, focusing at the examination site can be carried out easily and rapidly, and clear images can be acquired.

The first aspect described above may further include a transparent member disposed so as to close off a front-end opening of the cylindrical portion.

When the examination site is a soft material, such as an internal organ or the like, if the front-end opening were open, the examination site would enter the front-end opening in the cylindrical portion, thus making it impossible to ensure the proper the working distance. With the configuration described above, however, when the front end of the cylindrical portion abuts against the examination site, the transparent member disposed at the position where it closes off the front-end opening is pressed in close contact with the surface of the examination site. Therefore, the surface of the examination site is kept flat, which ensures the proper working distance. Accordingly, it is possible to align the focal position of the objective lens with a desired examination site merely by causing the front end of the cylindrical portion to abut against it, thus enabling rapid and straightforward acquisition of clear images.

In the configuration described above, the transparent member may be formed of a film member covering the front-end opening of the cylindrical portion. Furthermore, in the configuration described above, the transparent member may be formed of a cover glass secured to the front-end opening of the cylindrical portion.

The first aspect described above may further include an intermediate member provided so as to be movable in the optical axis direction relative to the support portion, wherein the cylindrical portion may be attached to the intermediate member in such a manner as to be attachable thereto and removable therefrom. By doing so, it is possible to replace only the cylindrical portion, which is inserted inside the body of a small laboratory animal or the like under examination and contacts the living organism. Therefore, by disposing of the cylindrical portion after use, it is possible to prevent contamination or infection and to omit a sterilization procedure.

In the first aspect described above, a securing member configured to secure the cylindrical portion to the examination target may be provided on the cylindrical portion.

With this configuration, after determining a site to be examined over time, it is possible to carry out examination of the same location on an examination target over time by securing the cylindrical portion to the examination target by operating the securing member.

The first aspect described above may further include a supply apparatus configured to supply liquid to the inside of the cylindrical portion. With this configuration, it is possible to make the objective lens function as an immersion objective lens. Because liquid is supplied inside the cylindrical portion by the operation of the supplying apparatus, the liquid fills the space between the narrow-diameter end portion and the cylindrical portion, thus ensuring a high numerical aperture and allowing bright images to be acquired.

A second aspect of the present invention is an objective lens unit including an objective lens having a narrow-diameter end portion; any one of the objective-lens guiding devices described above.

The present invention provides an advantage in that it is possible to easily locate the end face of the narrow-diameter end portion at a suitable position relative to the examination target without setting an examination site, thus enabling rapid and straightforward acquisition of an image of the examination site.

DETAILED DESCRIPTION OF THE INVENTION

Figure 1:
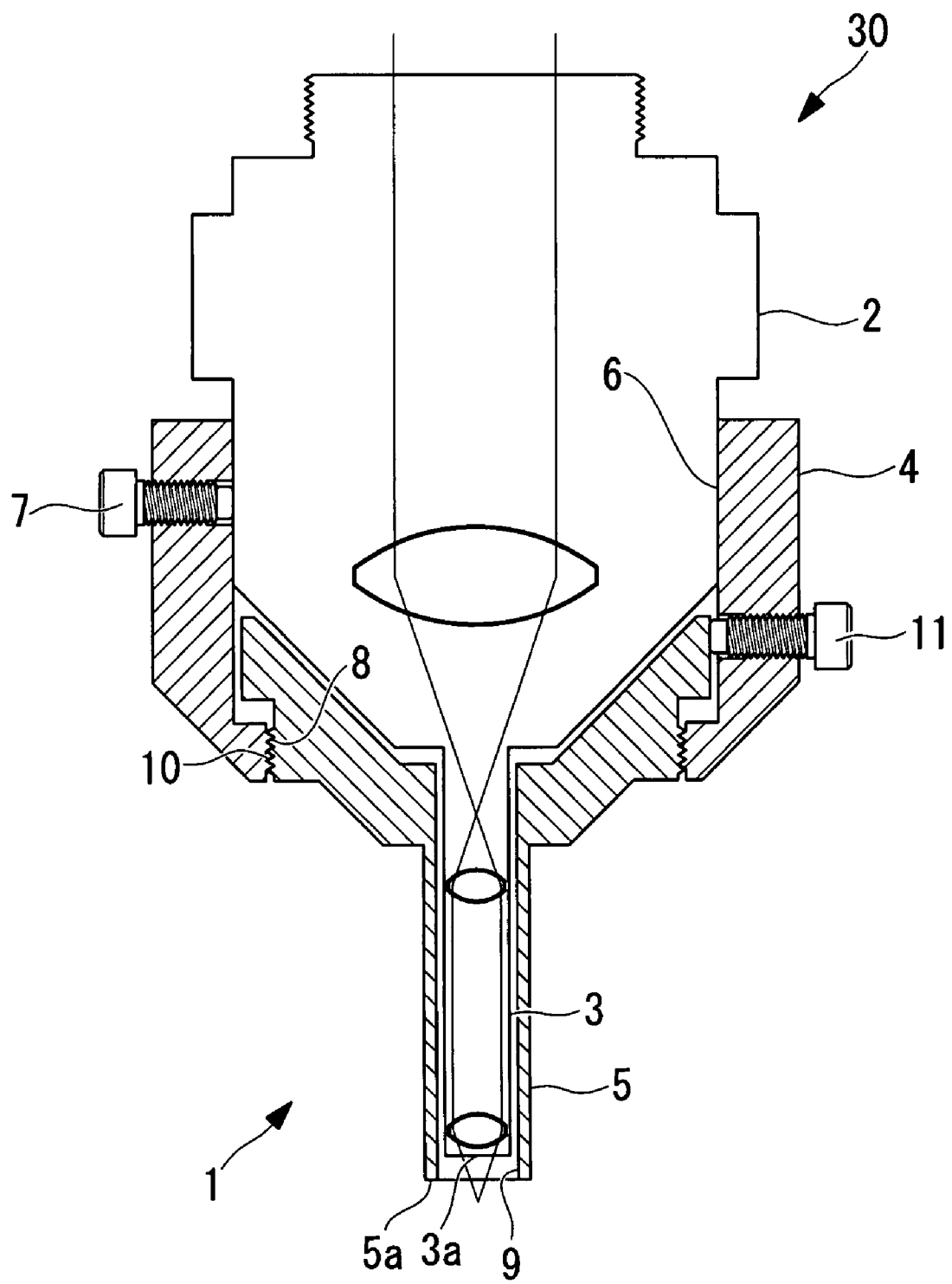
FIG. 1 is a longitudinal sectional view showing an objective-lens guiding device and an objective lens according to an embodiment of the present invention.

An objective-lens guiding device 1 and an objective lens unit 30 according to a first embodiment of the present invention will be described below with reference to FIG. 1.

The objective lens unit 30 according to this embodiment includes an objective lens 2 having a narrow-diameter end portion 3 and the objective-lens guiding device 1 attached to the objective lens 2. As shown in FIG. 1, the objective-lens guiding device 1 according to this embodiment, which is attached to the objective lens 2 having the narrow-diameter end portion 3, includes a support portion 4 which is secured to the objective lens 2 and a cylindrical portion 5 for accommodating the narrow-diameter end portion 3.

The support portion 4 includes a fitting portion 6 for fitting to the outer surface of the objective lens 2; a locking screw 7 for securing the support portion 4 to the objective lens 2 by pressing the outer surface of the objective lens 2 in the radial direction, with the fitting portion 6 fitted to the outer surface of the objective lens 2; and a female threaded portion 8 disposed at front side of the objective lens 2.

The cylindrical portion 5, which is a circular tube shaped member for accommodating the narrow-diameter end portion 3 of the objective lens 2, has an opening 9 (front-end opening) at the front end thereof and a male threaded portion 10 at the rear end that engages with the female threaded portion 8 of the support portion 4. Thus, when the cylindrical portion 5 is rotated about the central axis thereof, the cylindrical portion 5 is made to finely translate relative to the support portion 4 along the central axis by virtue of the engagement of the female threaded portion 8 and the male threaded portion 10.

The cylindrical portion 5 is preferably formed of a transparent material. Accordingly, the position of the narrow-diameter end portion 3 of the objective lens 2 accommodated inside the cylindrical portion 5 can be checked from outside.

Between the support portion 4 and the cylindrical portion 5, a locking screw 11 is provided for securing both of them at a suitable relative rotation.

The operation of the objective-lens guiding device 1 according to this embodiment, having such a configuration, will be described below.

With the objective-lens guiding device 1 according to this embodiment, by fitting the fitting portion 6 of the support portion 4 to the outer surface of the objective lens 2 and tightening the locking screw 7, the support portion 4 is secured to the objective lens 2. In this state, the cylindrical portion 5 engaged with the female threaded portion 8 of the support portion 4 accommodates the narrow-diameter end portion 3 of the objective lens 2, and a front end 5a of the cylindrical portion 5 is disposed farther toward the front than an end face 3a of the narrow-diameter end portion 3.

By loosening another locking screw 11 provided between the support portion 4 and the cylindrical portion 5, it is possible to rotate the cylindrical portion 5 about its axis relative to the support portion 4. Because the male threaded portion 10 of the cylindrical portion 5 is engaged with the female threaded portion 8 of the support portion 4, when the cylindrical portion 5 is rotated about the axis relative to the support portion 4, the cylindrical portion 5 is displaced along the optical axis relative to the support portion 4 by an amount determined by the lead of the threaded portions 8 and 10. Then, by tightening the locking screw 11; it is possible to secure the cylindrical portion 5 at a prescribed position relative to the support portion 4.

Because the working distance of the objective lens 2 is set in advance, by pre-adjusting the distance between the front end 5a of the cylindrical portion 5 and the end face 3a of the narrow-diameter end portion 3, it is possible to set in advance the focal position of the objective lens 2 when the front end 5a of the cylindrical portion 5 abuts against the examination target. In other words, by making the focal position of the objective lens 2 coincident with the position of the front end 5a of the cylindrical portion 5, it is possible to focus at the surface of the examination target against which the front end 5a of the cylindrical portion 5 abuts. Also, by placing the focal position of the objective lens 2 further towards the front than the position of the front end 5a of the cylindrical portion 5, it is possible to focus at a deeper position than the surface of the examination target against which the front end 5a of the cylindrical portion 5 abuts.

By doing so, simply by inserting the cylindrical portion 5 accommodating the narrow-diameter end portion 3 inside the body of the examination target, such as a small laboratory animal, and abutting the front end 5a of the cylindrical portion 5 against the examination site, such as an internal organ inside the body, it is possible to fix the focal position at a predetermined location with respect to the front end 5a of the cylindrical portion 5. Therefore, it is not necessary to perform focusing each time the examination site is searched for, thus enabling a clear image to be acquired rapidly.

Figure 2:
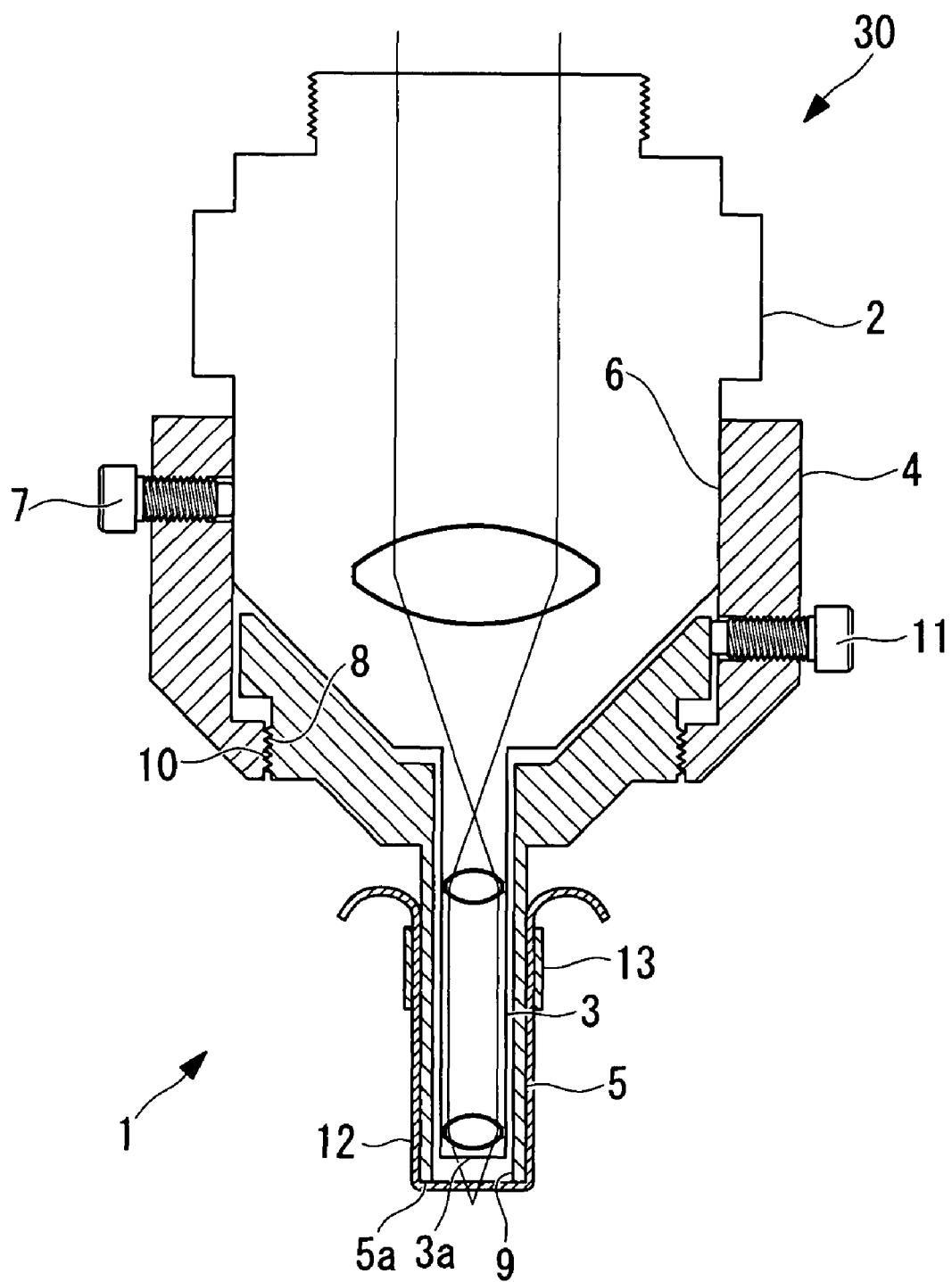
FIG. 2 is a longitudinal sectional view showing a first modification of the objective-lens guiding device in FIG. 1.

The objective-lens guiding device 1 according to this embodiment has been illustrated by a device in which the opening 9 at the front end 5a of the cylindrical portion 5 is open. However, when the examination site is relatively soft, the surface of the examination site bulges somewhat inside the opening 9 at the front end 5a, and in some cases, it is not possible to dispose the focal position at the desired location. Thus, as shown in FIG. 2, the opening 9a at the front end 5a of the cylindrical portion 5 is covered with a transparent film member (transparent member) 12 is disposed so as to stretch over the opening 9 to close it off. By doing so, during examination, the film member 12 is pushed in close contact with the surface of the examination site, which prevents it from bulging out. The film member 12 can be easily fixed to the cylindrical portion 5 by means of a rubber ring or heat-shrinkable tube 13, etc.

Figure 3:
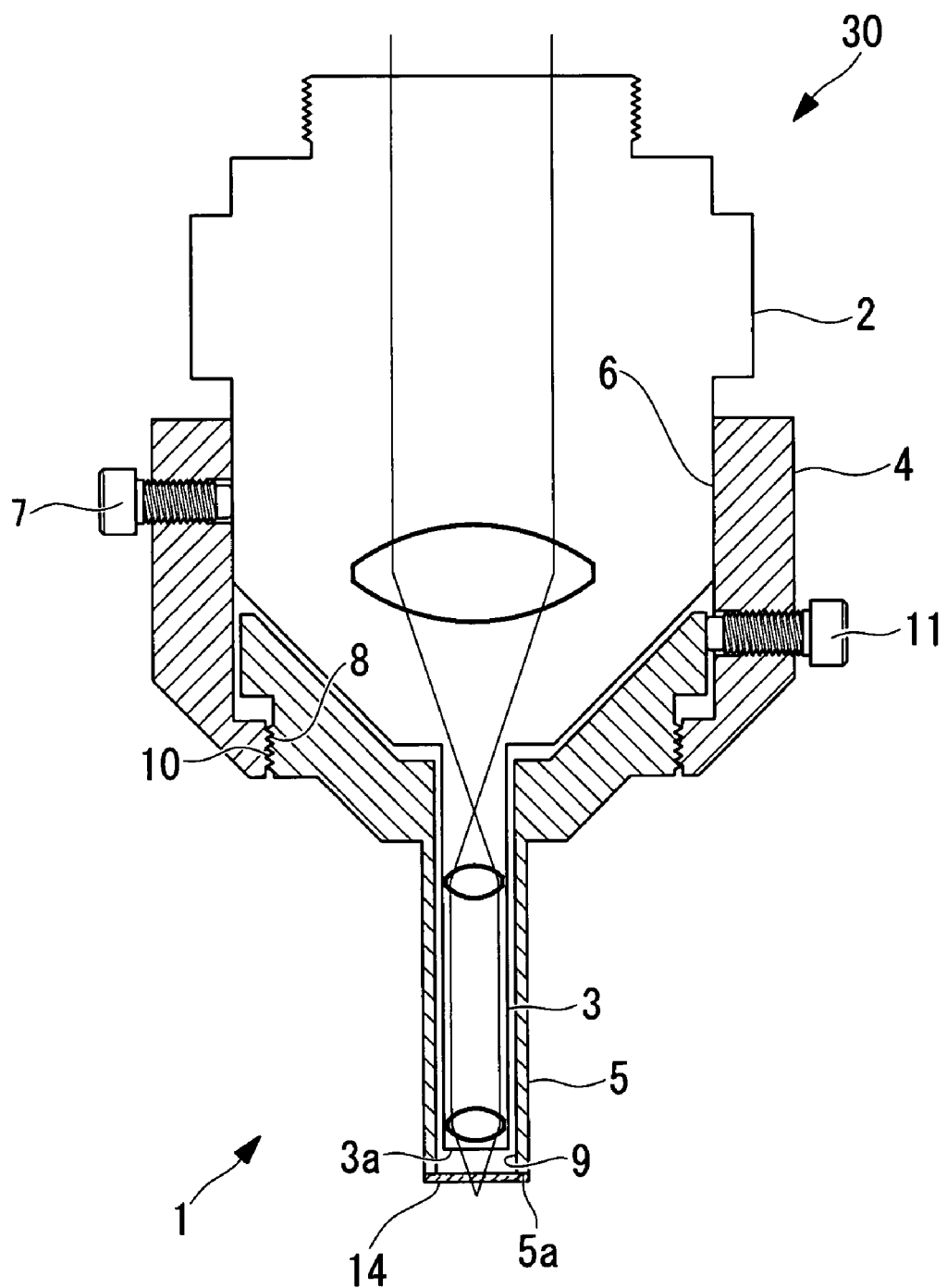
FIG. 3 is a longitudinal sectional view showing a second modification of the objective-lens guiding device in FIG. 1.

As shown in FIG. 3, instead of the film member 12, a cover glass 14 may be fixed to the opening 9 at the front end 5a of the cylindrical portion 5. With this configuration, because it is endowed with higher rigidity than the film member 12, it is possible to keep the surface of the examination site more flat. In this case, because it is not possible to make the cover glass 14 so thick, it is preferable to use sapphire glass, which has high strength.

Figure 4:
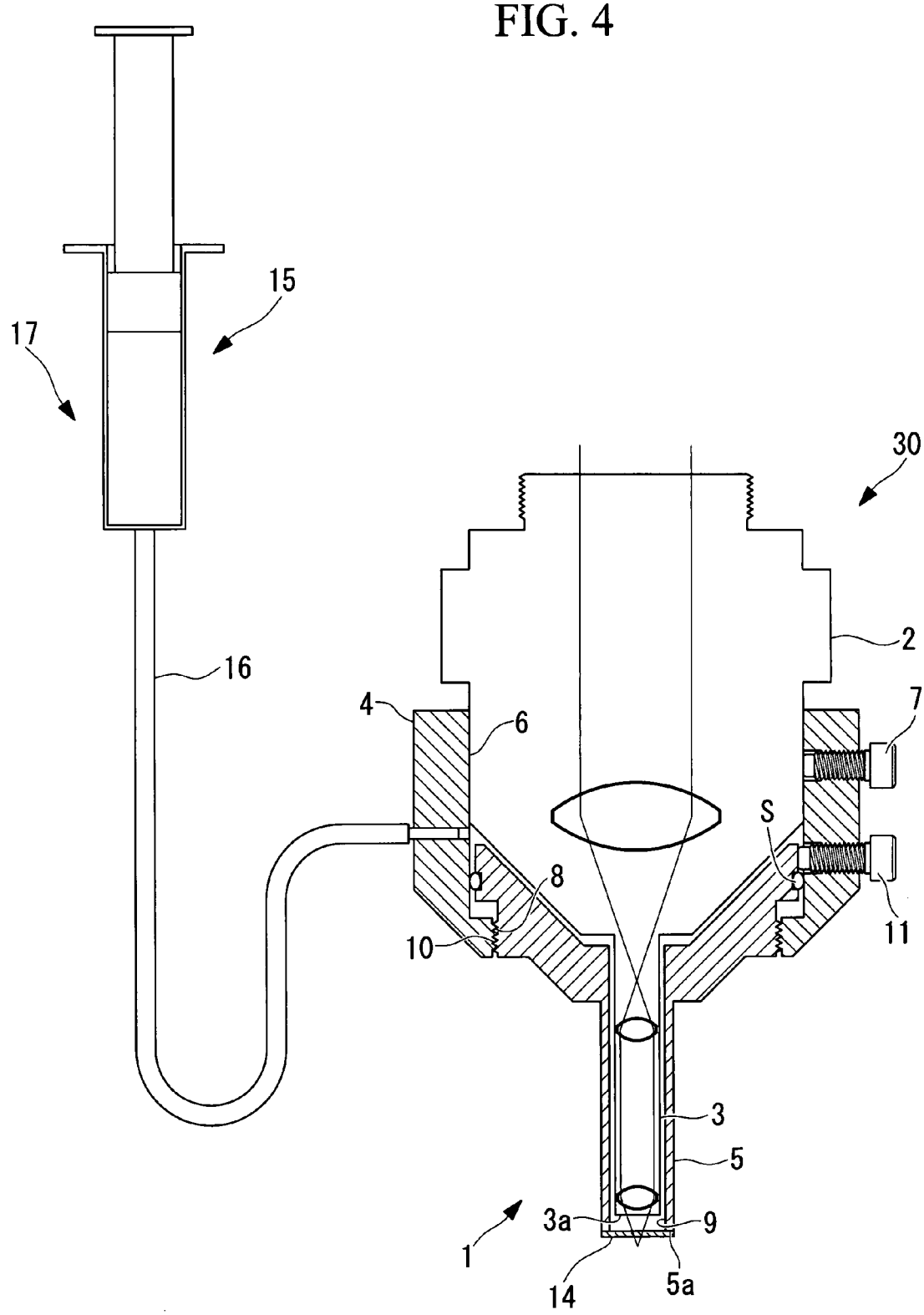
FIG. 4 is a longitudinal sectional view showing a third modification of the objective-lens guiding device in FIG. 1.

In this embodiment, as shown in FIG. 4, a liquid supply apparatus (supply apparatus) 17, formed, for example, of a syringe 15 and a tube 16, may be connected to the support portion 4 to supply a liquid inside the cylindrical portion 5. In this case, it is possible to construct an immersion objective lens by filling the gap between the examination site and the end face 3a of the narrow-diameter end portion 3 with a liquid, such as water or immersion oil, which increases the numerical aperture, thus enabling clearer images to be acquired. It is particularly preferable to use water as the liquid.

By fixing the tube 16 to the support portion 4, when the cylindrical portion 5 is rotated relative to the support portion 4 to adjust its position in the optical axis direction, the tube 16 does not move, thus facilitating replacement of the tube 16. Instead of this, it is possible to fix the tube 16 to the cylindrical portion 5 to function as a movable tube. In the drawing, reference symbols S is a sealing member for preventing leakage of liquid from between the support portion 4 and the objective lens 2 and from between the support portion 4 and the cylindrical portion 5.

Figure 5:
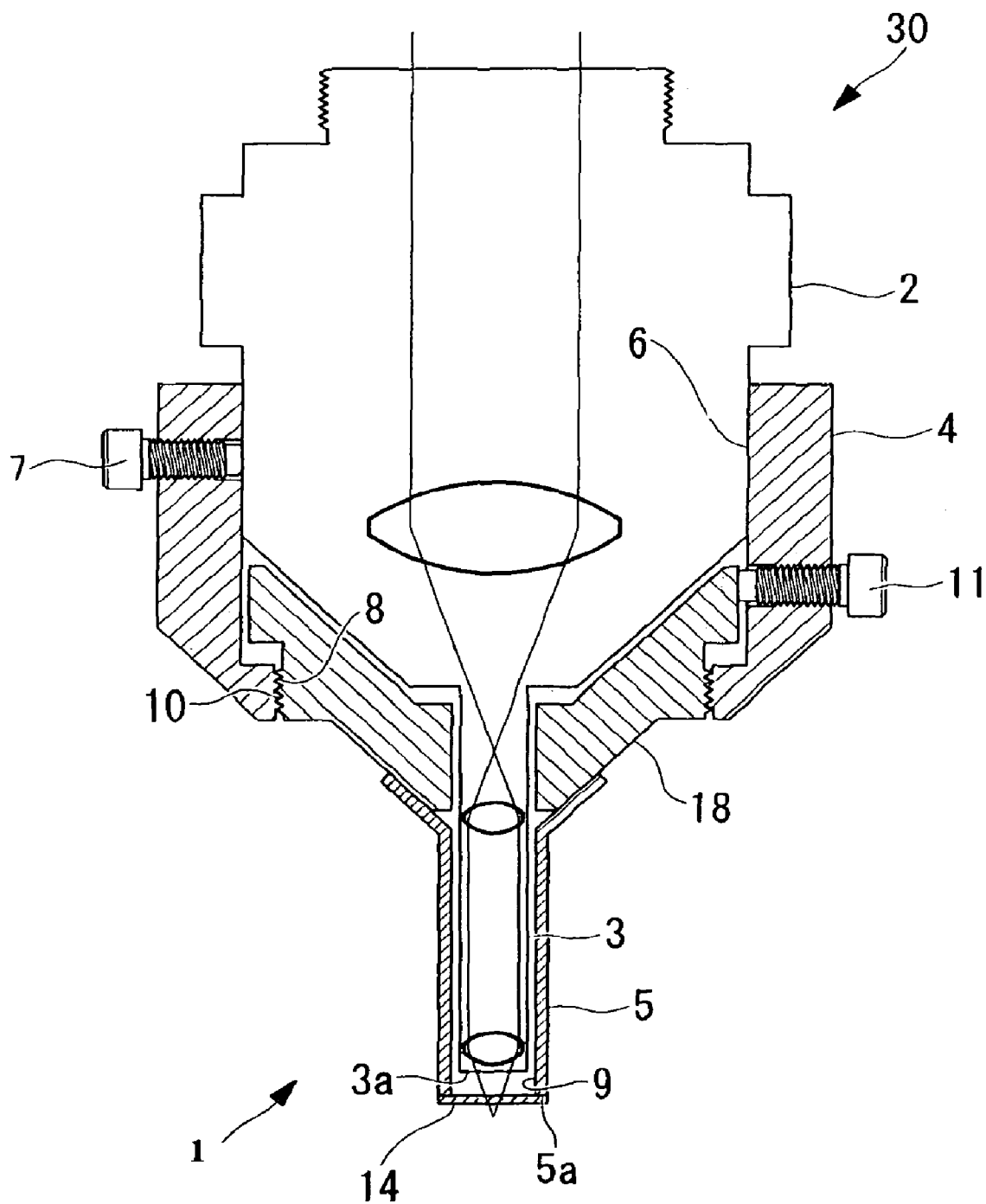
FIG. 5 is a longitudinal sectional view showing a fourth modification of the objective-lens guiding device in FIG. 1.

In this embodiment, the cylindrical portion 5 is formed of a single part. Instead of this, however, as shown in FIG. 5, it may be separated into a cylindrical portion 5 for accommodating the narrow-diameter end portion 3 of the objective lens 2 and an intermediate member 18 for connecting to the support portion 4, and the cylindrical portion 5 may be provided in such a manner as to be attachable to and detachable from the intermediate member 18. By doing so, the narrow-diameter end portion 3 is covered by the cylindrical portion 5 attached to the intermediate member 18, and only the cylindrical portion 5 is in contact with the living organism when the narrow-diameter end portion 3 is inserted inside the body of the living organism under examination, such as a small laboratory animal. Therefore, by removing the cylindrical portion 5 from the intermediate member 18 after examination and replacing it, the narrow-diameter end portion 3 is always covered by the cylindrical portion 5 and kept clean, which can prevent infection or contamination.

Figure 6:
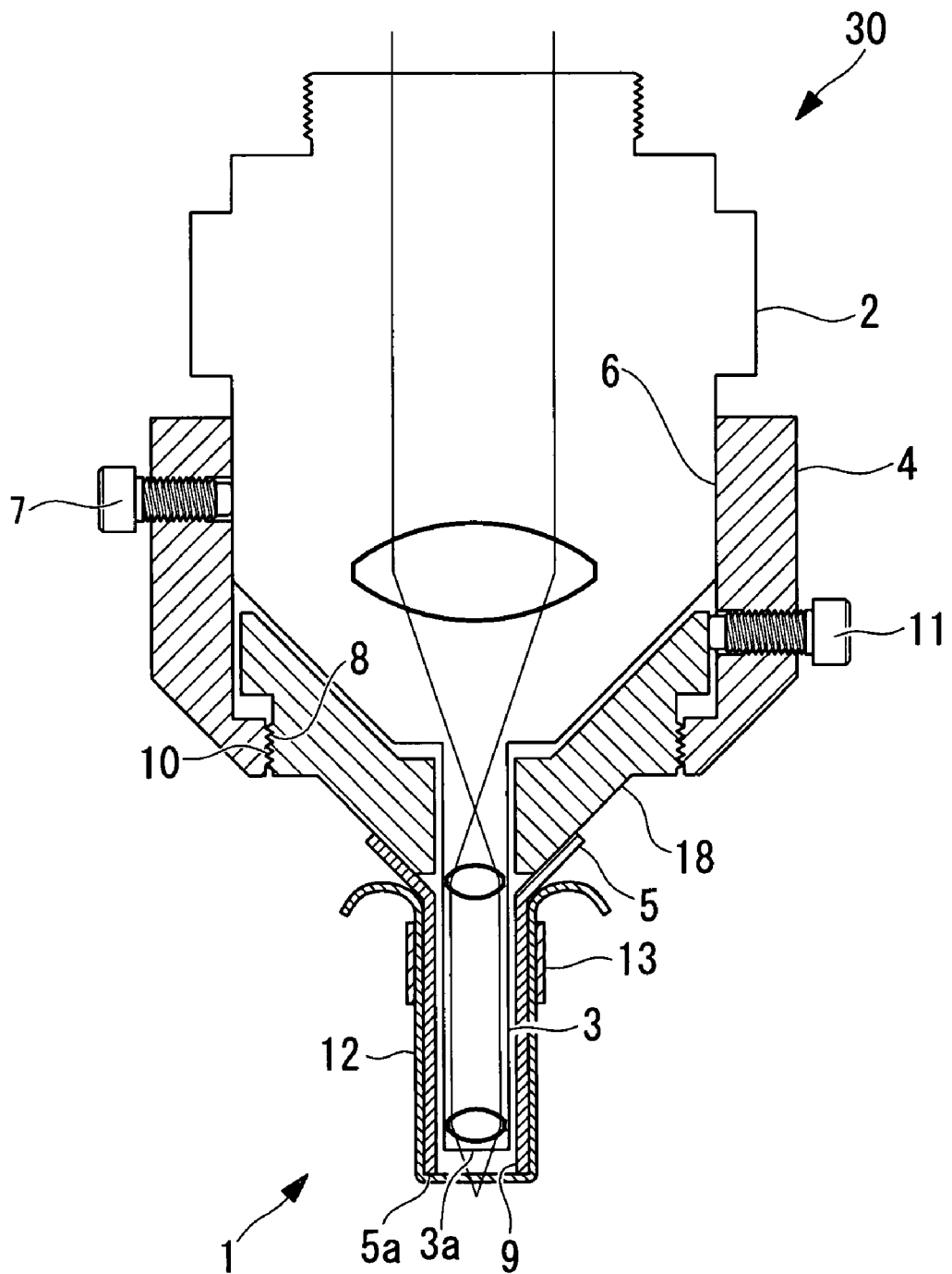
FIG. 6 is a longitudinal sectional view showing a fifth modification of the objective-lens guiding device in FIG. 1.

As shown in FIG. 6, instead of the cover glass 14 which is provided at the front end 5a of the cylindrical portion 5, the transparent film member 12 may be employed to cover and close off the opening 9 at the front end 5a of the cylindrical portion 5. By doing so, it is possible to attach and detach the film member 12 while the cylindrical portion 5 is removed from the intermediate member 18, which allows the working efficiency to be improved.

Figure 7:
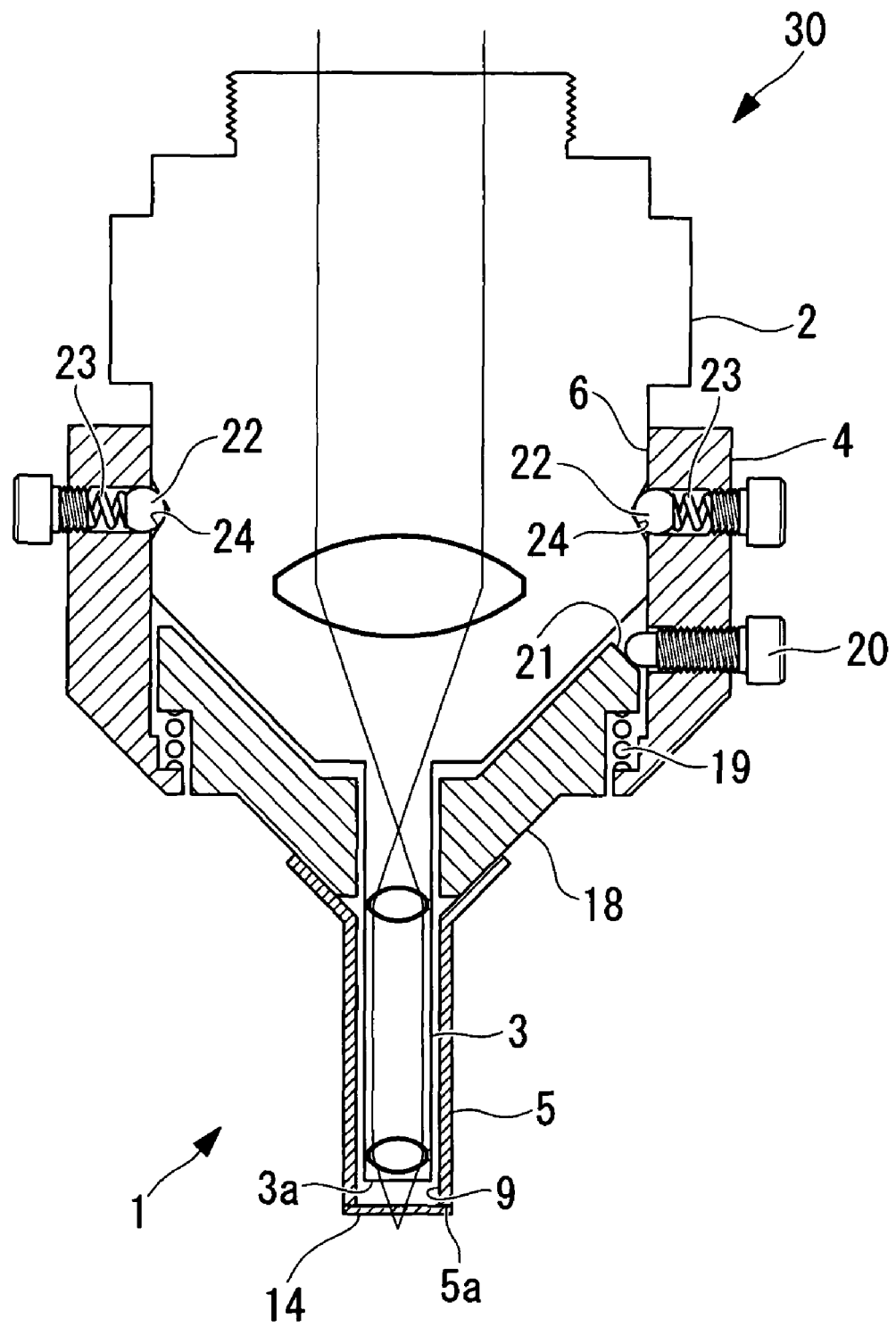
FIG. 7 is a longitudinal sectional view showing a sixth modification of the objective-lens guiding device in FIG. 1.

In this embodiment, by engaging the male threaded portion 10 provided on the cylindrical portion 5 or the intermediate member 18 with the female threaded portion 8 provided on the support portion 4, rotating the cylindrical portion 5 or the intermediate member 18 relative to the support portion 4 moves the cylindrical portion 5 or the intermediate member 18 in a direction along the optical axis. Instead of this, however, as shown in FIG. 7, by urging the cylindrical portion 5 with a coil spring 19 in a direction such that it retreats along the optical axis relative to the support portion 4 and by pressing a tapered surface 21 provided on the cylindrical portion 5 with a set screw 20 engaged with the support portion 4, it is possible to employ a configuration in which the cylindrical portion 5 is made to advance against an urging force of the coil spring 19.

The support portion 4 is secured to the objective lens 2 by the locking screw 7 in the configuration described above. Instead of this, however, it is possible to provide securing means such as a press-fit plunger or the like, having a ball 22 and a spring 23, as shown in FIG. 7. By doing so, when the fitting portion 6 of the support portion 4 is fitted to the objective lens 2, it engages with a hole 24 provided in the outer surface of the objective lens 2 due to the urging force of the ball 22 and the spring 23. Therefore, it is possible to secure the objective-lens guiding device 1 to the objective lens 2 with a single action.

Figure 8:
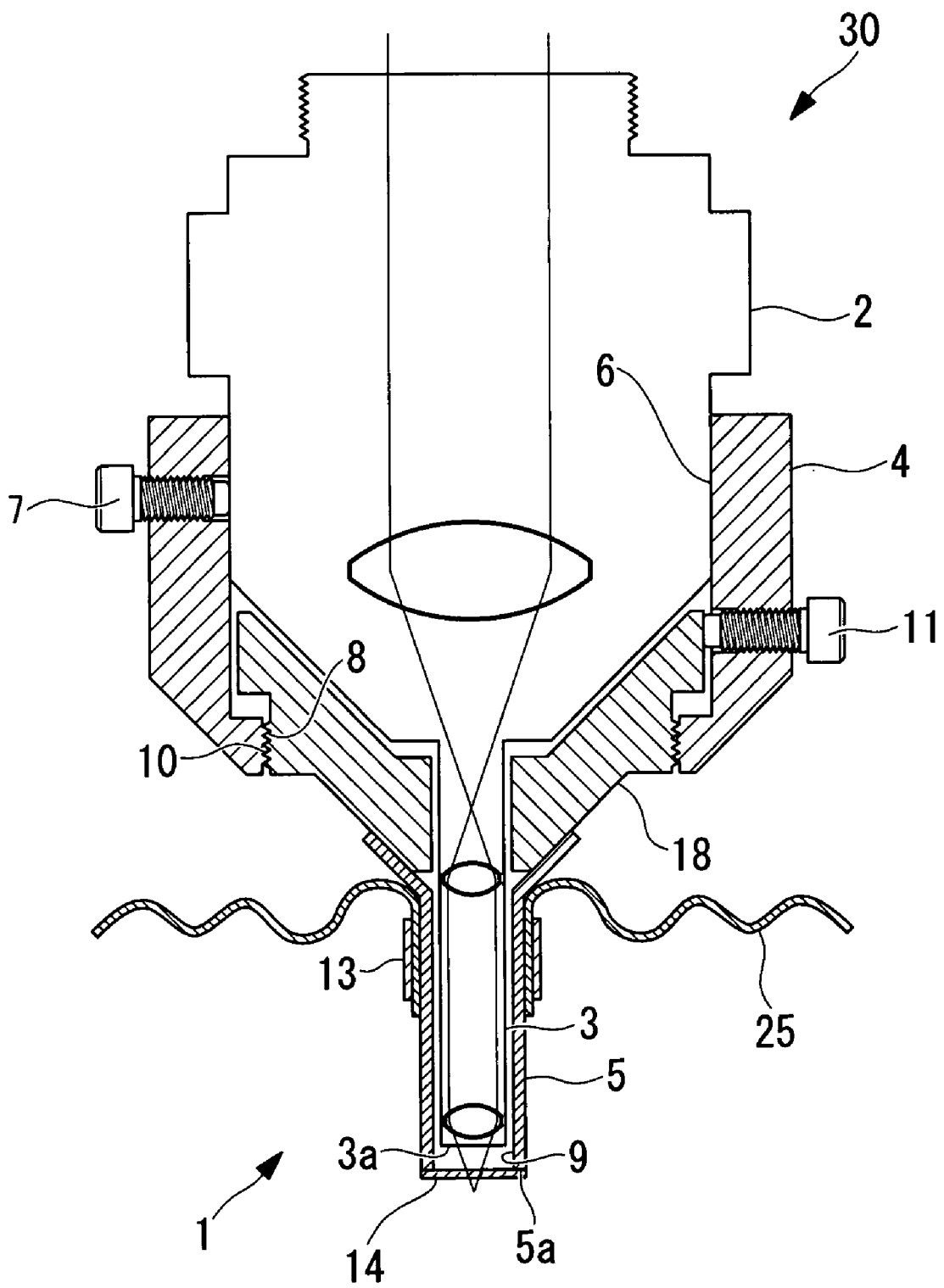
FIG. 8 is a longitudinal sectional view showing a seventh modification of the objective-lens guiding device in FIG. 1.

As shown in FIG. 8, a sheet member (securing member) 25 may be provided around the cylindrical portion 5 of the type that can be attached to and detached from the intermediate member 18. This sheet member 25 is formed of a biocompatible material, and it can be sewed to the skin of the small laboratory animal or the like under examination using, for example a needle and thread.

With this configuration, the sheet member 25 is not sewed to the skin until the examination site is set, thus allowing the cylindrical portion 5 to be freely moved, and improving the ease of use. In addition, by sewing the sheet member 25 to the skin after the examination site is set and securing the cylindrical portion 5, it is possible to continuously observe the same location.

In this case, because the cylindrical portion 5 is attached to the intermediate member 18 in such a manner that it can be attached and detached, after the examination site is set and the sheet member 25 is sewed to the skin, it is possible to remove the cylindrical portion 5 from the intermediate member 18 and leave the cylindrical portion 5 attached to the small laboratory animal under examination. Because the cylindrical portion 5 is extremely light since it covers just the narrow-diameter end portion 3, even when left attached, the free activity of the small laboratory animal or the like is not restricted. It is thus possible to perform examination over time while allowing normal activity of the small laboratory animal or the like.

The invention claimed is:

1. An objective-lens guiding device for guiding an objective lens having a narrow-diameter end portion at a distal end side and a large-diameter portion at a base end side, comprising:
   a support portion secured to the large-diameter portion,
   a cylindrical portion configured to accommodate the narrow-diameter end portion, and
   an intermediate member provided so as to be movable in the optical axis direction relative to the support portion, the intermediate member supporting the cylindrical portion so that the cylindrical portion is movable in the optical axis direction relative to the support portion,
   wherein a front end of the cylindrical portion is disposed at a location farther toward the front than an end face of the narrow-diameter end portion, and
   wherein the cylindrical portion is attached to the intermediate member in such a manner as to be attachable thereto and removable therefrom while maintaining relative positions of the objective lens and the support portion with respect to a position of the intermediate member.

2. An objective-lens guiding device according to claim 1, further comprising a transparent member disposed so as to close off a front-end opening of the cylindrical portion.

3. An objective-lens guiding device according to claim 2, wherein the transparent member is formed of a film member covering the front-end opening of the cylindrical portion.

4. An objective-lens guiding device according to claim 2, wherein the transparent member is formed of a cover glass secured to the front-end opening of the cylindrical portion.

5. An objective-lens guiding device according to claim 1, wherein a securing member configured to secure the cylindrical portion to an examination target is provided on the cylindrical portion.

6. An objective-lens guiding device according to claim 1, further comprising a supply apparatus configured to supply liquid to the inside of the cylindrical portion.

7. An objective lens unit comprising:
an objective lens having a narrow-diameter end portion; and
an objective-lens guiding device according to claim 1.

* * * * *